United States Patent [19]

Baier

[11] 4,350,170
[45] Sep. 21, 1982

[54] APPARATUS FOR MONITORING THE EXTERIOR OF A MOVING CIGARETTE ROD OR THE LIKE

[75] Inventor: Anton Baier, Wentorf, Fed. Rep. of Germany

[73] Assignee: Hauni-Werke Körber & Co. K.G., Hamburg, Fed. Rep. of Germany

[21] Appl. No.: 192,345

[22] Filed: Sep. 29, 1980

[30] Foreign Application Priority Data

Oct. 5, 1979 [DE] Fed. Rep. of Germany ....... 2940408

[51] Int. Cl.³ ........................... A24C 5/14; A24C 5/34
[52] U.S. Cl. .................................. 131/84 R; 131/906; 131/908; 131/910; 356/237; 250/227
[58] Field of Search ............... 131/280, 281, 282, 905, 131/906, 907, 908, 910, 84 R; 356/237; 250/227

[56] References Cited

U.S. PATENT DOCUMENTS

| | | | |
|---|---|---|---|
| 2,806,401 | 9/1957 | Demuth et al. | 356/237 |
| 3,068,742 | 12/1962 | Hicks, Jr. et al. | 250/227 |
| 3,695,771 | 10/1972 | Bardos | 356/237 |
| 3,746,575 | 7/1973 | Arnaudin et al. | 356/237 |
| 3,812,349 | 5/1974 | Gugliotta et al. | 356/237 |
| 3,818,223 | 6/1974 | Gibson et al. | 356/237 |

Primary Examiner—V. Millin

Attorney, Agent, or Firm—Kontler, Grimes & Battersby

[57] ABSTRACT

An apparatus for monitoring the exterior of a cigarette rod which moves lengthwise through an annular housing has a ring-shaped light-conducting prism which is mounted in the housing and is surrounded by an annulus of discrete light sources to direct testing light toward the exterior of a rod which moves therethrough. The prism directs light at an acute angle to the axis of the moving rod, and the light which is reflected by the exterior of the moving rod passes through an annulus of light conducting fibers each of which directs reflected light against a discrete photoelectronic transducer. The transducers form part of a circuit which evaluates the intensity of reflected light to thereby detect defects which cause an intensification or a weakening of reflected light. The prism has a triangular cross sectional outline with an apex of the outline adjacent to the path of the rod and a side which is located opposite the apex and extends at right angles to the direction of incident light. Such light issues at the apex and impinges upon the exterior of the moving rod. The latter is guided by an odd number of narrow webs which are installed at the rod-admitting end of the housing and are adjustable radially of the housing to engage rods of smaller or larger diameter.

18 Claims, 3 Drawing Figures

APPARATUS FOR MONITORING THE EXTERIOR OF A MOVING CIGARETTE ROD OR THE LIKE

BACKGROUND OF THE INVENTION

The present invention relates to apparatus for monitoring the condition and/or appearance of elongated rod-shaped articles which form part of or constitute the starting material for or are smokers' products. More particularly, the invention relates to improvements in apparatus for monitoring the exterior of a continuous or discontinuous rod-shaped commodity, such as a filter rod, a cigarette rod, a cigarillo rod, a cigar rod or the like.

It is already known to detect the presence of defects or blemishes of a continuous rod (such as a cigarette rod wherein a web of suitable wrapping material surrounds a rod-like filler consisting of natural, substitute and/or reconstituted tobacco) by causing the rod to pass through a ring-shaped housing which contains means for directing light against the exterior of successive increments of the rod. The rod reflects the light and the thus reflected light is evaluated by a suitable circuit. The results of evaluation are indicative of the condition and/or appearance of the corresponding portions or increments of the rod. It is also known to install in the housing a first light conducting device which directs incident light against the exterior of the running rod and a second light conducting device which directs reflected light against a transducer which generates signals denoting the intensity or another characteristic of reflected light. The signals can be indicative of a variety of defects of the rod (hereinafter referred to as cigarette rod). For example, a spot of adhesive will reflect more light than cigarette paper of which the envelope of a cigarette rod normally consists; therefore, the corresponding signal will indicate the presence of a defect which can be categorized as being of the strong light-reflecting type. On the other hand, a hole in the wrapper of a running rod will allow incident light to impinge upon and to be reflected by the relatively dark shreds of tobacco which form the filler of the cigarette rod; consequently, the intensity of reflected light will be lower and the evaluation of the corresponding signal will lead to the conclusion that the tested portion of the cigarette rod is unsatisfactory owing to the presence of a light-absorbing defect. The same holds true for creases, fold lines or smudges at the exterior of the wrapper. Furthermore, optical monitoring means can be utilized for detection of properly or improperly applied imprints in the form of lettering, symbols and/or a combination of these. Such imprints are customary on cigarettes to denote the name of the manufacturer, the brand name of the cigarette and/or the trademark or trademarks of the manufacturer or distributor. Certain imprints are made by resorting to light-absorbing paints or inks, and certain other imprints are made by resorting to bronze powder which reflects a relatively large quantity of incident light. The generation of regularly recurring signals in response to optical monitoring of a rod which is advanced at a given speed will indicate that the light-absorbing or light-reflecting imprints are properly positioned with reference to the planes in which the rod is to be severed to yield discrete cigarettes or analogous rod-shaped articles constituting or forming part of smokers' products. The absence of regularly recurring signals or the total absence of signals is indicative of undue shifting of the loci of application of imprints or of partial or total failure of the imprinting mechanism.

OBJECTS AND SUMMARY OF THE INVENTION

An object of the invention is to provide a relatively simple but highly reliable and rugged apparatus which can monitor a running rod of wrapped tobacco or the like in such a way that the signals which are generated in response to monitoring can be readily evaluated and classified to denote a wide variety of different types of defects or irregularities including one or more light-absorbing as well as one or more light-reflecting defects.

Another object of the invention is to provide the apparatus with novel and improved means for directing radiation against as well as for conveying reflected radiation from the exterior of a running cigarette rod or the like.

A further object of the invention is to provide the apparatus with novel and improved means for accurately testing large-diameter, medium-diameter or small-diameter rods.

An additional object of the invention is to provide the apparatus with novel and improved means for ascertaining the presence or absence of a wide variety of defects at the exterior of a cigarette rod or a like rod-shaped commodity which is caused to move axially at an elevated speed such as is necessary in a modern cigarette maker wherein plain cigarettes are turned out at the rate of up to and in excess of one hundred per second.

Still another object of the invention is to provide an apparatus whose reliability greatly exceeds that of heretofore known apparatus, which is relatively inexpensive and can be installed in all or nearly all existing machines serving to manufacture and/or process rod-shaped articles constituting or forming part of smokers' products, and which requires a minimum of attention during long periods of continuous or intermittent use.

Another object of the invention is to provide a testing or monitoring apparatus which can be combined with or incorporated in a relatively simple evaluating circuit to furnish signals which denote the presence or absence of creases, folds or holes in the wrappers of cigarette rods or the like, the presence of spots consisting of adhesive or other strongly light-reflecting material on the wrapper of a running rod confining a filler of tobacco or the like, the presence or absence of light-absorbing and/or light-reflecting imprints on the web, the presence of regularly or irregularly distributed imprints, and/or the presence of smudges and/or particles of foreign matter at the exterior of the running rod.

The invention resides in the provision of an apparatus for monitoring the exterior of rod-shaped smokers' products which move lengthwise along a predetermined path (e.g., toward the cutoff in a cigarette rod making machine). The apparatus comprises first light conducting means defining a first light path which makes an oblique angle (e.g., an angle of approximately 45 degrees) with the axis of the moving product, a plurality of discrete light-emitting diodes or other suitable means for admitting light to the first light conducting means so that incident light which passes through the first light conducting means impinges upon and is reflected at the exterior of the moving product at a second oblique angle which is a function of the first oblique angle (if the first oblique angle is 45 degrees, the second oblique angle is also 45 degrees), and second light conducting means which is located in the path of and is arranged to conduct light that is reflected by the moving product. The second light conducting means can direct reflected light to discrete photoelectronic transducers which form part of an evaluating circuit serving to ascertain the intensity of reflected light and hence the condition and/or appearance of the corresponding portions of the exterior of the moving product. If the intensity of reflected light is excessive, this can denote the presence of a shiny or strongly light-reflecting portion of the wrapper of a cigarette if the moving product is a cigarette rod. If the intensity of reflected light is below a preselected threshold value, this can indicate the presence of a hole in the wrapper of the cigarette rod.

The apparatus preferably further comprises an annular housing for the light admitting means and for the two light conducting means. The housing defines an opening which extends substantially axially thereof and through which the product moves lengthwise. The first light conducting means directs light toward the axis and the second light conducting means directs reflected light away from the axis of the moving product.

At least the first light conducting means may constitute an annulus which surrounds a portion of the opening in the housing, and such annulus may constitute a prism having a substantially triangular cross-sectional outline. The outline of each cross-section through the prism (each such cross-section includes the axis of the prism) has a point or apex close to the moving rod-shaped product and a side which is located opposite the point and is remote from the moving product. Such sides of plural cross-sections of the prism preferably constitute or lie in a frustoconical surface of the prism and the light-admitting means may include an annulus of discrete light sources which are adjacent to the frustoconical surface. The light sources direct light at right angles to the frustoconical surface and through the prism so that incident light emerges at the points or apices and thereupon impinges upon successive increments of the exterior of the moving product.

The novel features which are considered as characteristic of the invention are set forth in particular in the appended claims. The improved apparatus itself, however, both as to its construction and its mode of operation, together with additional features and advantages thereof, will be best understood upon perusal of the following detailed description of certain specific embodiments with reference to the accompanying drawing.

DESCRIPTION OF THE PREFERRED EMBODIMENTS

Figure 2:
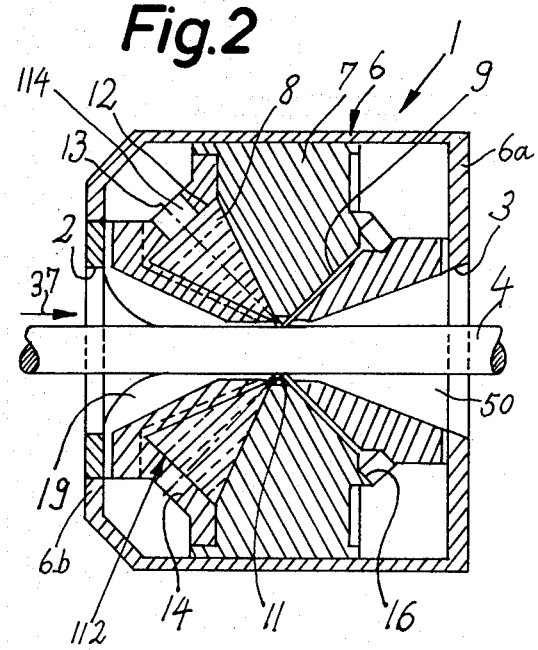
FIG. 2 is an axial sectional view as seen in the direction of arrows from the line II—II of FIG. 1.
Figure 1:
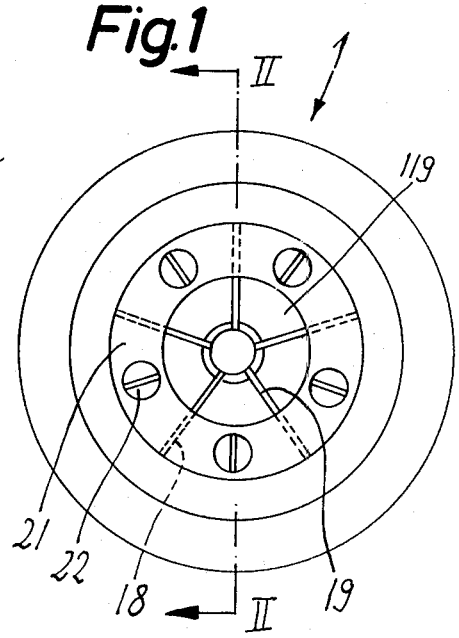
FIG. 1 is a schematic end elevational view of an apparatus which embodies the invention.

The apparatus 1 which is shown in FIGS. 1 and 2 comprises a ring-shaped housing 6 which is a hollow cylindrical shell and confines a composite annular mounting block 7. The end walls 6b and 6a of the housing 6 are respectively provided with an inlet 2 and an outlet 3 respectively constituting the foremost and rearmost portions of an axially extending opening 50 through which the rod 4 to be monitored is caused to move axially in the direction indicated by an arrow 37. The housing 6 can be installed in a cigarette rod making machine, e.g., in a cigarette maker known as Garant which is manufactured by the assignee of the present application. In a cigarette maker, the housing 6 will be installed between the wrapping mechanism and the customary cutoff which latter severs the rod so that the rod yields a file of discrete plain cigarettes of unit length or multiple unit length. The means for moving the rod 4 lengthwise in the direction of the arrow 37 includes the customary garniture of the cigarette maker.

The mounting block 7 supports a ring-shaped light conducting prism 8 which serves to direct light against the exterior of the running rod 4 in the housing 6, i.e., while the rod 4 advances through the opening 50. The prism 8 causes light to travel in a direction toward the axis of the running rod 4, and the exterior of the rod (i.e., the exterior of the tubular wrapper of the rod) reflects incident light in a direction toward the housing 6, i.e., away from the axis of the rod. The mounting block 7 further supports a second light conducting device 9 which consists of an annulus of light conducting fibers each having a light-admitting end close to the exterior of the rod 4 in the opening 50 and a light-discharging end which is disposed at a greater distance from the path of the rod 4. The exact manner in which the fibers or filaments of the light conducting device 9 are installed in the block 7 and/or the manner of installing the prism 8 in this block forms no part of the present invention.

Figure 3:
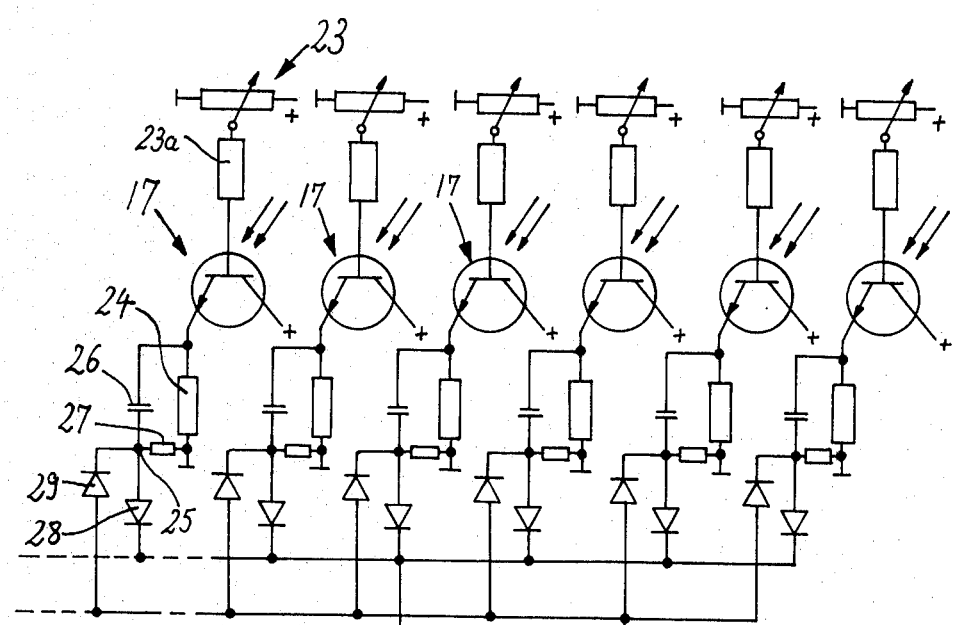
FIG. 3 is a diagram of a portion of an evaluating circuit which receives signals from the apparatus of FIGS. 1 and 2.
Figure 3:
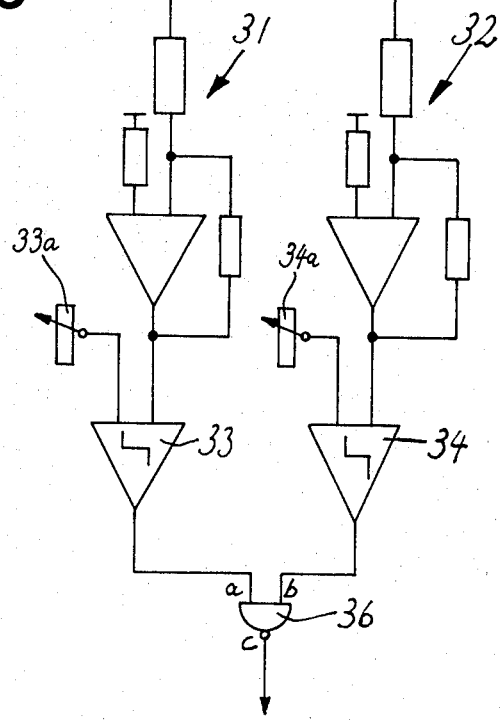

As shown in FIG. 2, each axial section through the light conducting prism 8 has a triangular outline with one side (12) of the triangle remote from the path of the running rod 4 and the point or tip 11 opposite the side 12 adjacent to the exterior of the rod. Means is provided for admitting light to the prism 8 in such a way that the light rays travel at right angles to the sides 12 toward and through the tips 11 to be reflected by the exterior of the rod 4 and to thereupon penetrate into the light-admitting ends of the filaments or fibers of the light-conducting device 9. The path of one of the beams of incident light is indicated in FIG. 2 by a phantom line 13 which halves the angle at the tip 11 and extends at right angles to the side 12. The sides 12 of the sum of all axial sections through the prism 8 lie on a frustoconical external surface 112 of the prism 8. The sum of lines 13 constitutes the generatrix of the path of beams of incident light which is admitted by an annulus of discrete light sources 114 installed in apertures or holes 14 provided in the mounting block 7 adjacent to the frustoconical surface 112. Each light source 114 may constitute a light emitting diode. In the illustrated apparatus, the angle of incidence is 45 degrees and the angle of reflection of light at the exterior of the running rod 4 is also 45 degrees. Thus, the filaments or fibers of the downstream light conducting device 9 (as considered in the direction of the arrow 37) are positioned and oriented in such a way that they allow reflected light to pass therethrough, and each filament or fiber of the device 9 directs some of the reflected light against the light-sensitive surface of a discrete photosensitive transistor 17 six of which are shown in FIG. 3. These transistors 17 are installed in the apertures or holes 16 of the mounting block 7 adjacent to the light-discharging ends of the respective fibers.

It will be readily appreciated that the light conducting device 9 can be replaced with other suitable light conducting means, e.g., with a prism which is a mirror image of the prism 8 with reference to a plane extending at right angles to the axis of the running rod 4. It is further clear that the continuous running rod 4 can be replaced with a composite rod, e.g., with a file of discrete plain cigarettes (in such instance, the apparatus of FIG. 1 and 2 is installed downstream of the aforementioned cutoff in the cigarette maker).

In the illustrated embodiment of the apparatus 1, the mounting block 7 is formed with sixteen apertures 14 for an equal number of discrete light sources 114 of the light admitting means, and with sixteen apertures 16 for discrete photosensitive transducers 17. The apertures 14 and 16 are respectively equidistant from each other, as considered in the circumferential direction of the housing 6, and form two annuli which respectively surround the frustoconical surface 112 and the light discharging ends of filaments or fibers of which the light conducting device 9 consists.

The apparatus 1 further comprises means for accurately guiding the rod 4 during axial or lengthwise movement through the opening 50 of the housing 6. Such guide means includes an odd number (e.g., five) of relatively narrow projections in the form of thin ribs or webs 19 installed in radially extending slits 18 of the mounting block 7. The illustrated webs 19 are installed in the mounting block 7 partially within the confines of the prism 8 and in the region of the inlet 2 where successive increments of the rod 4 enter the housing 6. If desired, similar guide means can be provided at the other end of the housing 6, i.e., in the region of the outlet 3. The neighboring webs 19 and the neighboring slits 18 are equidistant from each other, as considered in the circumferential direction of the rod 4.

When the illustrated rod 4 is followed by a rod having a larger or smaller diameter, the positions of the webs 19 can be adjusted by resorting to a calibrating mandrel having an outer diameter matching that of the rod to be introduced into the opening 50, and the webs 19 are thereupon fixed and maintained in newly selected positions by a ring-shaped holder 21 which is separably secured to the housing 6 by a plurality of screws 22, bolts or analogous fasteners.

If the rod 4 is not a perfect cylinder or its outline deviates considerably from such configuration, portions of the unround or deformed rod can penetrate into the recesses 119 between neighboring webs 19 of the guide means.

An important advantage of the guide means including the webs 19 is that the apparatus 1 can be rapidly and conveniently converted for the monitoring of rods having different diameters and that such conversion does not necessitate the replacement of any parts, i.e., one and the same set of webs 19 can be used to adequately guide rod-shaped commodities having different diameters. The relatively small number of webs 19 contributes to lower cost of the apparatus.

A portion of the evaluating circuit which includes the aforementioned photosensitive transducers 17 and serves to process the signals which are furnished by the fibers of the light conducting device 9 is shown in FIG. 3. Each transducer 17 is connected with an adjustable potentiometer 23 which can select the operating point of the respective transducer by way of a resistor 23a. The emitters of the transducers 17 are connected with resistors 24 which are connected in parallel with capacitors 26 adapted to discharge by way of resistors 27. Each junction 25 between a capacitor 26 and the respective resistor 27 is connected with two diodes 28 and 29. Each diode 28 transmits a positive (bright) signal which is generated in response to increased reflection of incident light by a portion of the exterior of the running rod 4. Each diode 29 serves to transmit (negative) signals in the opposite direction, i.e., to transmit (dark) signals which are generated in response to reflection of light upon light-absorbing portions of the exterior of the rod 4.

The diodes 28 are connected with a common operational amplifier 31 for "bright" signals, and the diodes 29 are connected with a common operational amplifier 32 for "dark" signals. The outputs of the operational amplifiers 31 and 32 are respectively connected with the right-hand inputs of two discrete comparators 33 and 34 which are further connected with sources 33a, 34a of reference signals, e.g., with adjustable potentiometers. The arrangement is such that the output of the comparator 33 transmits a signal to the input a of an OR gate 36 when the intensity of signal at the right-hand input of the comparator 33 exceeds a preselected threshold value which is determined by the intensity of the reference signal furnished by the source 33a. Analogously, the output of the comparator 34 transmits a signal to the other input b of the OR gate 36 when the intensity of a signal transmitted to the right-hand input of this comparator is less than a predetermined threshold value selected by the source 34a.

If the exterior of the running rod 4 exhibits a relatively bright portion (such as an adhesive-containing splice between two successive webs which are united in the cigarette maker in a manner well known from the art and not forming part of the present invention), the bright portion moves along the innermost portion of the ring-shaped prism 8 and causes a more pronounced reflection of light beams which are admitted to and pass through the prism 8 along a path indicated by the broken line 13. Such light beams are reflected by the bright portion of the exterior of the rod 4 and penetrate through one or more fibers of the light conducting device 9 (depending on the size and/or shape of the bright spot) to impinge upon the corresponding transistor or transistors 17 of the evaluating circuit shown in FIG. 3. Therefore, the outputs of such transistors 17 transmit voltage signals of corresponding (greater) intensity. Such change in the intensity of voltage signals at the output or outputs of one or more transistors 17 causes the associated capacitors 26 to discharge and the diodes 28 allow electric currents to flow to the input of the operational amplifier 31 which is designed to respond to "bright" signals. The amplified signal is transmitted to the corresponding input of the comparator 33 which compares such signal with the respective reference signal (potentiometer 33a) and transmits a signal to the input a of the OR gate 36 when the magnitude of the signal which is transmitted by the amplifier 31 exceeds the preselected threshold value. This causes the output c of the OR gate 36 to transmit a signal to a device (e.g., a nozzle for discharge of a jet of compressed air) which ejects the corresponding (defective) plain cigarette when the latter reaches an ejecting station. The manner in which defective cigarettes can be ejected in a cigarette maker in response to "defect" signals furnished by a logic circuit or by a time-delay device (e.g., a shift register) serving to delay the signals in imitation of the speed of travel of the corresponding portion of the cigarette rod to the ejecting station as well known from the art of cigarette making. The ejection can take place on a drum-shaped conveyor which follows the aforementioned cutoff and serves to convert a file of discrete coaxial plain cigarettes into one or more rows wherein the cigarettes move sideways, e.g., into a filter tipping machine of the type known as MAX S (manufactured by the assignee of the present application).

When the rod 4 exhibits a hole or another light-absorbing portion, such portion advances in the direction of the arrow 37 and reaches the light-emitting innermost portion of the prism 8. The intensity of light which is reflected by tobacco shreds inwardly of the hole in the wrapper of the rod 4 is less pronounced than the intensity of light which is reflected by cigarette paper or like wrapping material. Therefore, the corresponding signals are transmitted to the operational amplifier 32 via diodes 29 which block the transmission of "bright" signals. The amplifier 32 amplifies such signals and transmits them to the comparator 34 which transmits a signal to the input b of the OR gate when the nature of the light-absorbing portion of the rod 4 warrants segregation of the corresponding article from satisfactory or presumably satisfactory articles. In the just mentioned instance, the photosensitive transducers 17 receive weaker light signals and transmit correspondingly weaker voltage signals. Such change in the magnitude or intensity of signals transmitted by one or more transducers 17 in response to detection of a hole or another light-absorbing portion of the rod 4 will again cause a discharge of the corresponding capacitor or capacitors 26 with the result that the thus generated signals are transmitted to the amplifier 32. The negative potential at the minus sides of the respective diodes 29 then causes the flow of current in a direction counter to that via diodes 28. The comparator 34 transmits a signal when the intensity of signal which is transmitted by the amplifier 32 is less than the preselected threshold value. This causes the OR gate 36 to transmit a signal to the aforementioned ejecting device which segregates the defective cigarette from satisfactory articles as soon as the defective cigarette reaches the ejecting station.

An important advantage of the improved apparatus is that the aforediscussed mounting of light conducting devices 8 and 9 in the housing 6 allows for selection of a definite common reflection zone or region in the opening 50. This renders it possible to generate scatter-free signals with a high degree of accuracy and reliability so that the signals can be used for predictable segregation of articles exhibiting a wide variety of defects some of which entail a more pronounced and some of which entail a less pronounced reflection of light by the exterior of the rod 4. In other words, the apparatus enables the evaluating circuit of FIG. 3 or an analogous evaluating unit to generate highly reliable "dark" or "bright" signals so that the number of satisfactory articles which are ejected and/or the number of defective articles which are not ejected is much lower than in machines which utilize conventional monitoring apparatus.

The circumferentially complete one-piece annular prism 8 can be replaced by a light conducting device which consists of an annulus of several discrete sections together forming a ring which surrounds a portion of the opening 50 in the housing 6. The illustrated cirumferentially complete prism 8 is preferred at this time because it has been found that, in combination with an annulus of light sources 114 around the surface 112 of the prism, the apparatus 1 ensures a maximum light output and a high concentration of incident light which impinges upon successive annular increments of the exterior of the running rod 4. Thus, the distribution of light which issues at the tips or points 11 of the triangular cross-sectional outlines of the prism 8 is uniform all the way around the running rod 4 and the malfunctioning or total failure of one or more light sources 114 does not result in localized reduction of intensity of light which impinges upon the rod 4. On the contrary, the distribution of light which issues from the prism 8 to impinge upon the rod 4 remains unchanged; only the intensity of such light decreases as a function of the number of defective or disconnected light sources 114. It has also been found that the failure of one or more light sources 114 (as long as the number of such light sources is within reasonable limits) entails a hardly discernible reduction of the intensity of light which issues from the prism 8. Uniform distribution of light which issues from the prism 8 is desirable and advantageous because this ensures that each and every portion of each successive annular region of the exterior of the running rod 4 is illuminated to the same degree.

Another important advantage of the improved apparatus 1 is the provision of adjustable means (webs 19) for guiding the rod 4 at least in the region of the inlet 2 of the opening 50. This ensures that the testing conditions remain ideal or practically ideal even if the rod 4 exhibits portions whose configuration deviates from a circular outline and even if such outline is quite different from a true circular or cylindrical outline. The webs 19 ensure that the distance between each portion of the exterior of the rod 4 (as considered in the circumferential direction of the rod) and the innermost portion of the prism 8 remains constant or practically constant; this, in turn, ensures the establishment of the aforementioned ideal or nearly ideal testing conditions. The webs 19 eliminate any play between the rod 4 and the housing 6 in the region where the innermost portion of the prism 8 surrounds the rod. As mentioned above, the relatively small number of webs 19 contributes to simplicity of the apparatus and renders it possible to provide a requisite number of relatively large recesses 119 into which the material of the rod 4 can penetrate or yield if the outline of a portion of the rod is not that of a true cylinder. The same holds true if the diameter of the rod 4 at times exceeds the predetermined or contemplated diameter, namely, the diameter of that mandrel or an equivalent calibrating tool which has been used to adjust the webs 19, as considered in the radial direction of the housing 6, prior to application of the ring 21 and fasteners 22.

Without further analysis, the foregoing will so fully reveal the gist of the present invention that others can, by applying current knowledge, readily adapt it for various applications without omitting features that, from the standpoint of prior art, fairly constitute essential characteristics of the generic and specific aspects of my contribution to the art and, therefore, such adaptations should and are intended to be comprehended within the meaning and range of equivalence of the appended claims.

I claim:

1. Apparatus for monitoring the exterior of rod-shaped smokers' products which move lengthwise, comprising first light conducting means defining a first light path making a first oblique angle with a line perpendicular to the axis of the moving product; means for admitting light to said first light conducting means so that light which passes through said first light conducting means impinges upon and is reflected by the exterior of the moving product at a second oblique angle which is a function of said first oblique angle; second light conducting means located in the path of and arranged to conduct light which is reflected by the moving produce; and an annular housing for said light conducting means, said housing having a substantially axially extending opening for the moving product.

2. The apparatus of claim 1, wherein said first light conducting means is arranged to conduct light toward the axis and said second light conducting means is arranged to conduct reflected light away from the axis of said housing.

3. The apparatus of claim 2, wherein said first light conducting means is an annulus which surrounds a portion of said opening.

4. The apparatus of claim 3, wherein said first light conducting means comprises a prism having a substantially triangular cross-sectinal outline, said outline having a point adjacent to and a side located opposite and remote from said opening, said light admitting means being arranged to admit light to said prism in a direction at right angles to said side and through said prism so that light which impinges upon the exterior of and is reflected by the moving product issues from said prism at said point.

5. The apparatus of claim 4, wherein said prism has a frustoconical surface and said side of each cross section of said prism is located in said frustoconical surface.

6. The apparatus of claim 4, wherein said light admitting means comprises a plurality of discrete light sources forming an annulus around said prism.

7. The apparatus of claim 6, wherein said light sources include light-emitting diodes.

8. The apparatus of claim 4, wherein said direction makes an angle of approximately 45 degrees with the axis of the moving product.

9. The apparatus of claim 2, wherein said opening has a product-admitting inlet and a product-discharging outlet, and further comprising means for guiding the moving product in said opening, at least in the region of said inlet.

10. The apparatus of claim 9, wherein said means for guiding comprises projections mounted in said housing and extending radially inwardly toward the axis of the moving product.

11. The apparatus of claim 10, wherein said projections are narrow webs which are spaced apart from each other, as considered in the circumferential direction of said housing.

12. The apparatus of claim 11, wherein said means for guiding comprises an odd number of webs with recesses between neighboring webs.

13. The apparatus of claim 11, wherein said means for guiding comprises five webs.

14. The apparatus of claim 10, wherein said projections are movable substantially radially of said housing between a plurality of different positions so as to guide the exteriors of moving products having different diameters.

15. The apparatus of claim 14, further comprising means for fixing said projections in selected positions with reference to said housing.

16. The apparatus of claim 2, wherein said housing comprises a substantially cylindrical shell and an annular mounting member in said shell, said light conducting means and said light admitting means being installed in said mounting means.

17. Apparatus for monitoring the exterior of rod-shaped smokers' products which move lengthwise, comprising first light conducting means defining a first light path making a first oblique angle with a line perpendicular to the axis of the moving product; means for admitting light to said first light conducting means so that light which passes through said first light conducting means impinges upon and is reflected by the exterior of the moving product at a second oblique angle which is a function of said first oblique angle; and second light conducting means located in the path of and arranged to conduct light which is reflected by the moving product, one of said light conducting means comprising an annulus of light conducting filaments.

18. Apparatus for monitoring the exterior of rod-shaped smokers' products which move lengthwise, comprising first light conducting means defining a first light path making a first oblique angle with a line perpendicular to the axis of the moving product; means for admitting light to said first light conducting means so that light which passes through said first light conducting means impinges upon and is reflected by the exterior of the moving product at a second oblique angle which is a function of said first oblique angle; and second light conducting means located in the path of and arranged to conduct light which is reflected by the moving product, each of said light conducting means constituting an annulus surrounding the moving product and said second light conducting means being disposed downstream of said first light conducting means, as considered in the direction of lengthwise movement of the product.

* * * * *